United States Patent
Gantt

(10) Patent No.: US 6,598,236 B1
(45) Date of Patent: Jul. 29, 2003

(54) HEADGEAR COOLING AND PROTECTIVE AIR FLOW SYSTEM

(76) Inventor: Tracy R. Gantt, 3703 Annewakee Rd., Douglasville, GA (US) 30135

( * ) Notice: Subject to any disclaimer, the term of this patent is extended or adjusted under 35 U.S.C. 154(b) by 0 days.

(21) Appl. No.: 09/694,156

(22) Filed: Oct. 23, 2000

Related U.S. Application Data

(60) Provisional application No. 60/161,031, filed on Oct. 25, 1999.

(51) Int. Cl.$^7$ ................................................. A42C 5/04
(52) U.S. Cl. ................... 2/171.3; 2/8; 2/906; 2/DIG. 1; 132/53
(58) Field of Search .................. 2/171.3, 8, 7, 424, 2/209.13, 906, DIG. 1, 5; 132/53

(56) References Cited

U.S. PATENT DOCUMENTS

| | | | |
|---|---|---|---|
| 3,566,409 A | * | 3/1971 | Hopper .................... 2/171.3 X |
| 4,095,289 A | | 6/1978 | Kissen et al. |
| 4,133,308 A | * | 1/1979 | Lowe et al. ............. 2/171.3 X |
| 4,498,202 A | * | 2/1985 | Yamamoto .................... 2/424 |
| 4,502,480 A | | 3/1985 | Yamamoto |
| 4,752,974 A | | 6/1988 | Haino |
| 4,998,415 A | | 3/1991 | Larsen |
| 5,016,287 A | | 5/1991 | Harris |
| 5,085,231 A | * | 2/1992 | Johnson ................... 2/171.3 X |
| 5,123,114 A | * | 6/1992 | Desanti .............................. 2/8 |
| 5,146,757 A | | 9/1992 | Dearing |
| 5,353,605 A | * | 10/1994 | Naaman .................. 2/171.3 X |
| 5,715,533 A | * | 2/1998 | Stein .................................. 2/7 |
| 5,867,999 A | | 2/1999 | Bratton et al. |
| 6,032,291 A | * | 3/2000 | Asenguah et al. ........... 2/171.3 |
| 6,050,099 A | | 4/2000 | Lopa et al. |
| 6,125,636 A | | 10/2000 | Taylor et al. |

\* cited by examiner

Primary Examiner—Peter Nerbun
(74) Attorney, Agent, or Firm—Bernstein & Associates, P.C.; Jason A. Berstein

(57) ABSTRACT

The present invention relates to that of an incorporated cooling system that is incorporated into headgear that would be worn by a user. The cooling system of the present invention comprises a plurality of hollow plastic tubes all interconnected to one another. The plastic tubes serve both as a means in which an even distribution of air flow occurs over a user's head and also serves as a skeletal framework for the particular piece of headgear which the present invention is associated with. Air flow through the present invention occurs throughout the plastic tubes by the presence of air compressor unit, which is mounted on the particular piece of headgear in an inconspicuous place. The air compressor unit is powered by a power means. The plastic tubes of the present invention have inwardly facing air outlet holes that solely but steadily blow air onto the head of an individual wearing a piece of headgear with the present invention.

14 Claims, 4 Drawing Sheets

HEADGEAR COOLING AND PROTECTIVE AIR FLOW SYSTEM

This application claims the bnefit of provisional application Ser. No. 60/161,031 filed Oct. 25, 1999.

BACKGROUND OF THE INVENTION

The present invention relates to that of an incorporated cooling system, and more particularly relates to an incorporated cooling system which is incorporated into a wide variety of headgear.

DESCRIPTION OF THE PRIOR ART

U.S. Pat. No. 6,125,636, issued to Taylor et al., discloses a self-contained personal cooling and/or heating device which includes a heat dissipating member that fits around a portion of a user's body to be thermally regulated.

U.S. Pat. No. 6,050,099, issued to Lopa et al., discloses a device for installing in a cap and dispensing a cooing medium onto the head of its wearer.

U.S. Pat. No. 5,867,999, issued to Bratton et al., discloses an evaporative cooling band device adapted to be positioned upon a user's body.

U.S. Pat. No. 5,146,757, issued to Dearing, discloses a helmet cooling system which has a receptacle containing a coolant through which air flows, impelled by the velocity of the vehicle on which the system is used.

U.S. Pat. No. 5,016,287, issued to Harris, discloses an evaporative cooled cloth hood worn wet for use in high temperature atmospheres comprising a plurality of parts which when secured together fit over the head, forehead and chest of the user for cooling purposes.

U.S. Pat. No. 4,998,415, issued to Larsen, discloses a body cooling apparatus for removing body or external heat in an environment where sufficient cooling by perspiration is not available.

U.S. Pat. No. 4,752,974, issued to Haino, discloses an air-feed type protective helmet which includes a cap body to which a face shield is rotatably mounted for movement between a lower use position and an upper non-use position.

U.S. Pat. No. 4,502,480, issued to Yamamoto, discloses a helmet comprising a face shield and a device for supplying atmospheric air to the interior of the helmet.

U.S. Pat. No. 4,095,289, issued to Kissen et al., discloses an air ventilation apparatus for a flight helmet having a member secured to the helmet and having portion spaced from the helmet to form a plenum chamber and exit nozzle.

SUMMARY OF THE INVENTION

The present invention relates to that of an incorporated cooling system that is incorporated into headgear that would be worn by a user. The cooling system of the present invention would comprise a plurality of hollow plastic tubes all interconnected to one another. The plastic tubes would serve both as a means in which an even distribution of air flow would occur over a user's head and would also serve as a skeletal framework for the particular piece of headgear which the present invention would be associated with. Air flow through the present invention would occur throughout the plastic tubes by the presence of air compressor unit, which would be mounted on the particular piece of headgear in an inconspicuous place. The air compressor unit would be powered by a power means. The plastic tubes of the present invention would have inwardly facing air outlet holes that would solely but steadily blow air onto the head of an individual wearing a piece of headgear with the present invention.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved incorporated cooling system that is incorporated into headgear that would be worn by a user which has all of the advantages of the prior art and none of the disadvantages.

It is another object of the present invention to provide a new and improved incorporated cooling system that is incorporated into headgear that would be worn by a user which may be easily and efficiently manufactured and marketed.

It is still another object of the present invention to provide a new and improved incorporated cooling system that is incorporated into headgear that would be worn by a user which is of durable and reliable construction.

It is another object of the present invention to provide a new and improved incorporated cooling system that is incorporated into headgear that would be worn by a user which is economically affordable and available to the buying public.

It is another object of the present invention to provide a new and improved incorporated cooling system that is incorporated into headgear that would be worn by a user which is lightweight and convenient to use.

Other objects, features and advantages of the present invention will become more readily apparent from the following detailed description of the preferred embodiment when considered with the attached drawings and appended claims.

DESCRIPTION OF THE PREFERRED EMBODIMENTS

Figure 1:
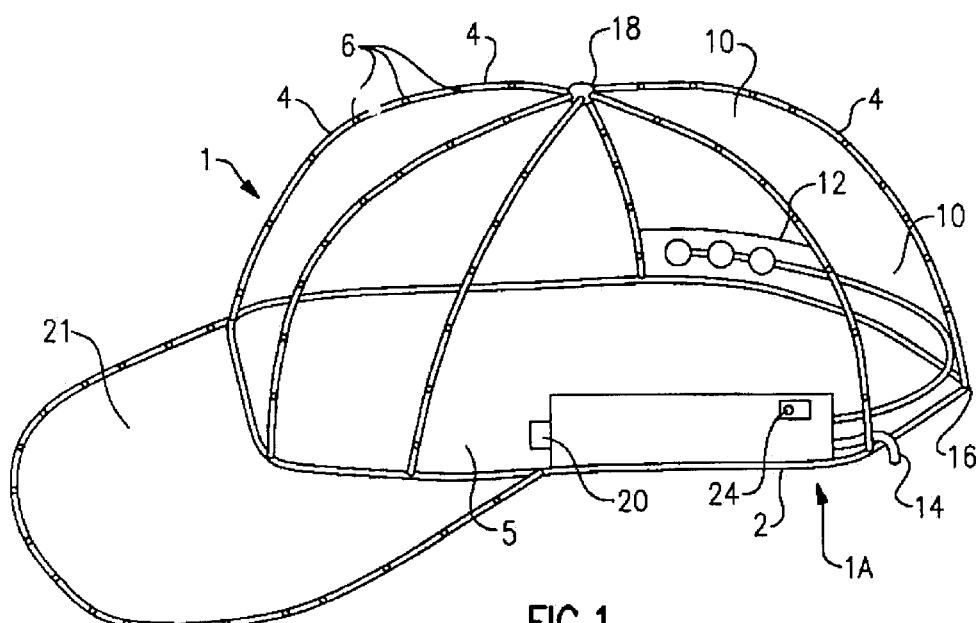
FIG. 1 is a perspective view of the present invention in use with a baseball cap.
Figure 2:
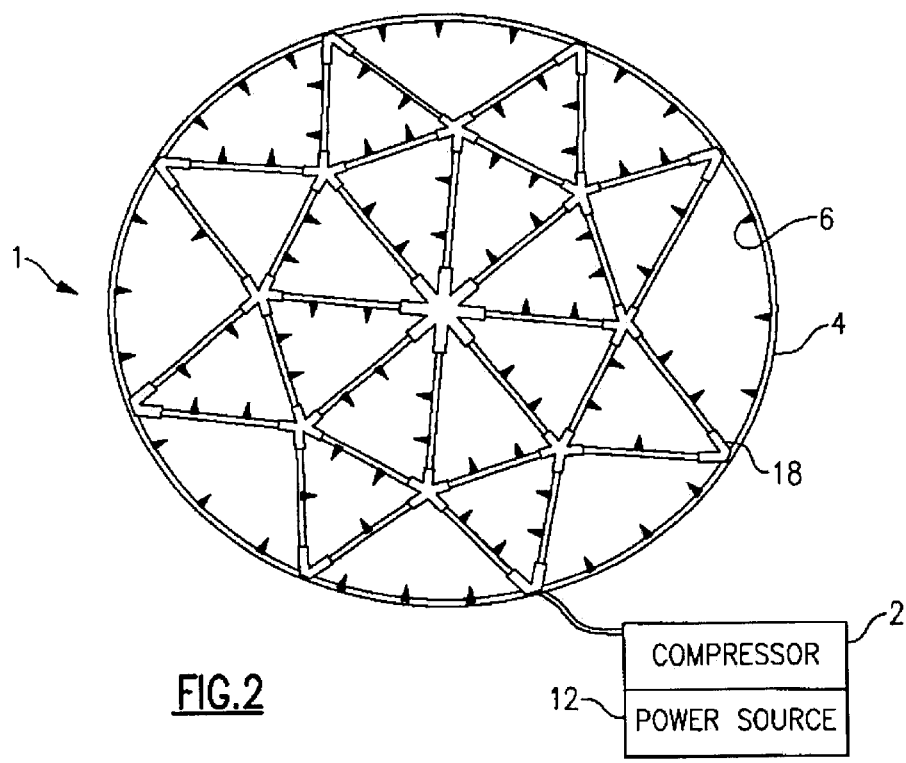
FIG. 2 is a perspective view of the present invention in use with a helmet.

FIGS. 1 through 8 all represent possible applications of the present invention. The particular uses as shown in these figures are by no means meant to be limiting, as the present invention could be used with other types of headgear not currently mentioned or fathomed by the inventor.

The primary use of the present invention can be as a cooling system 1 for headgear 5 that can be worn by a user in a wide variety of applications and situations. The cooling system 1 of the present invention comprises a plurality of hollow plastic tubes 4 with each plastic tube 4 being connected to at least one other plastic tube 4. The plurality of hollow plastic tubes 4 can form an interconnected network of hollow plastic tubes. The plurality of hollow plastic tubes 4 of the present invention can, in all embodiments, permit an even distribution of air flow to be blown onto the head of a user. In some of the embodiments, the plurality of hollow plastic tubes 4 serve as a skeletal framework for the particular piece of headgear 5 with which the cooling system 1 of the present invention can be associated.

A plastic connector 18 connects two or more adjacent pieces of plastic tubes 4. Each plastic connector can also be hollow and allows air flow to continue uninterrupted throughout the two or more adjacent plastic tubes 4. There can be various embodiments of plastic connector 18 that can be used in conjunction with the present invention, with the embodiments varying depending on how many plastic tubes can be interconnected to each other at each particular junction.

Whether the plurality of hollow plastic tubes 4 can serve as a skeletal framework in a particular framework in a particular piece of headgear 5 depends on the material 10 from which the particular piece of headgear 5 can be fabricated. Where the headgear 5 is made of cotton or other fabric, the plurality of hollow plastic tubes can play a more important skeletal framework role than if the material 10 is plastic or some other hard substance.

Air flow occurs in the present invention throughout the plurality of hollow plastic tubes 4 due to the presence of an air compressor unit 2, which can be inconspicuously mounted on the particular piece of headgear 5, such as a baseball cap 1A, shown in FIG. 1. The air compressor unit 2 can be powered by power means 12. Power means 12 can preferably is at least one battery which can also be mounted in an inconspicuous place on the headgear 5. Alternatively, power means 12 can be connected to air compressor unit 2 via an electronic connection 16 which can properly transmit power from power means 12 to air compressor unit 2.

Air compressor unit 2 can also have an on-off switch 24 which can turn the power on or off for air compressor unit 2. In addition, air compressor unit 2 can also have intake air tube 14 to allow air to be properly taken into air compressor unit 2 and pumped through the plurality of hollow plastic tubes 4.

In order to ensure that air flow in the cooling system 1 occurs evenly over a user's head while wearing a specific headgear 5, the plurality of hollow plastic tubes 4 has a plurality of evenly spaced-out air outlet holes 6. Each air outlet hole 6 is inwardly facing the location of where a user's head can be. Once air compressor unit 2 can be turned on, as long as an adequate air supply is present, air compressor unit 2 can blow air through the network of hollow plastic tubes 4 with the result that air can evenly blow out in an even distribution throughout the plurality of air outlet holes 6 located on the hollow plastic tubes 4.

Some embodiments of the present invention have a diverter switch 20 attached to the air compressor unit 2. The diverter switch 20 is be present on only those embodiments that can have an extra flap 21, such as a hat brim or bill. Generally, flap 21 is used to distinguish an extra overhand portion of a piece of headgear 5, such as a cowboy hat brim (see FIG. 8) or the bill of a baseball cap 1A (see FIG. 1).

In those embodiments of the present invention that can include diverter switch 20, an extra set of plastic tubes 4 can be present on the borderline or edge of the extra flap 21 that can be present. In normal operation, air flow would not occur through these extra plastic tubes 4 that would be located around the perimeter of the extra flap 21 present. However, if a user decided to use the diverter switch 20, extra air can then be pumped through the hollow tubes 4 located around the perimeter of the flap 21. The extra hollow tubes 4 around the perimeter of flap 21 can be designed to not necessarily cool the top of a user's head, but can have a more immediate effect on the user's face and the back of their head, including the neck area. The diverter switch 20 can be a multi-positional switch which can permit this to happen.

Figure 3:
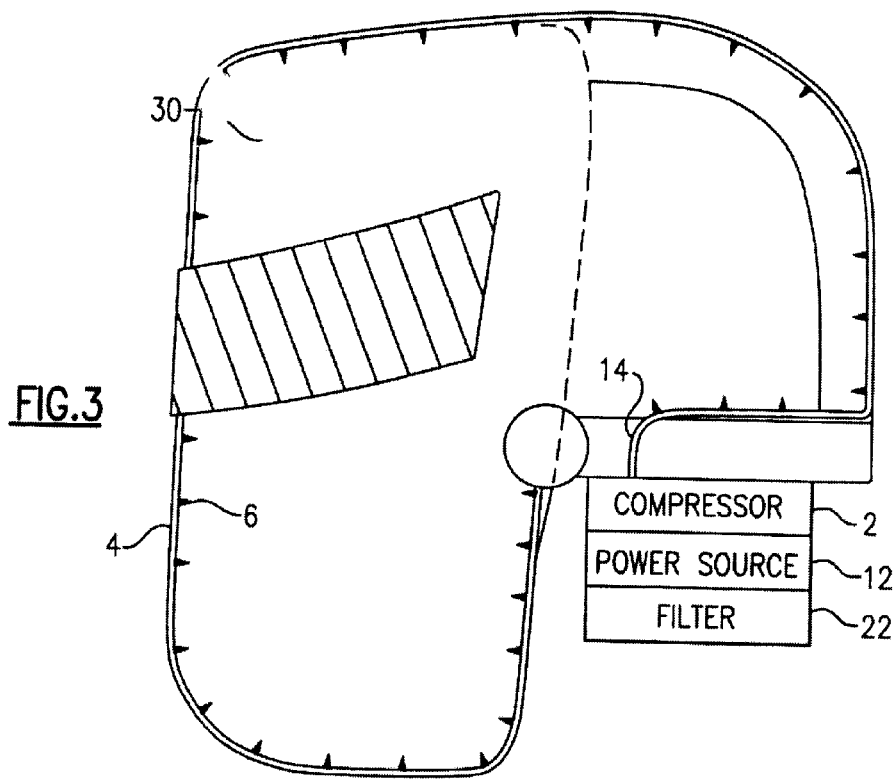
FIG. 3 is a perspective view of the present invention in use with a welder's mask.

In other various embodiments of the present invention, a filter 22 can be present (see, for example, FIG. 3). Filter 22 can be attached to the beginning of the intake air tube 14 in certain instances in which it can be desirous to filter air before it can be sucked into the compressor unit 2 and travel through the plurality of hollow plastic tubes 4. Embodiments of the present invention in which filter 22 may be appropriate can be a welder's mask 30 (FIG. 3), a hardhat 40 (see FIG. 6), and a cowboy hat (see FIG. 8). For a hardhat 40 the power means 12 and the air compressor unit 2 can optionally be constructed somewhat larger because the hardhat can be strapped to the user's head. The airflow can be diverted from inside the hardhat 40 to the brim 21 to direct debris away from the face. In these specific types of embodiments, a user can experience dust, smoke, and other types of airborne irritants that should clearly be filtered out before surrounding air is sucked into air compressor unit 2 to be distributed through the hollow plastic tubes 4 on headgear 1.

Figure 4:
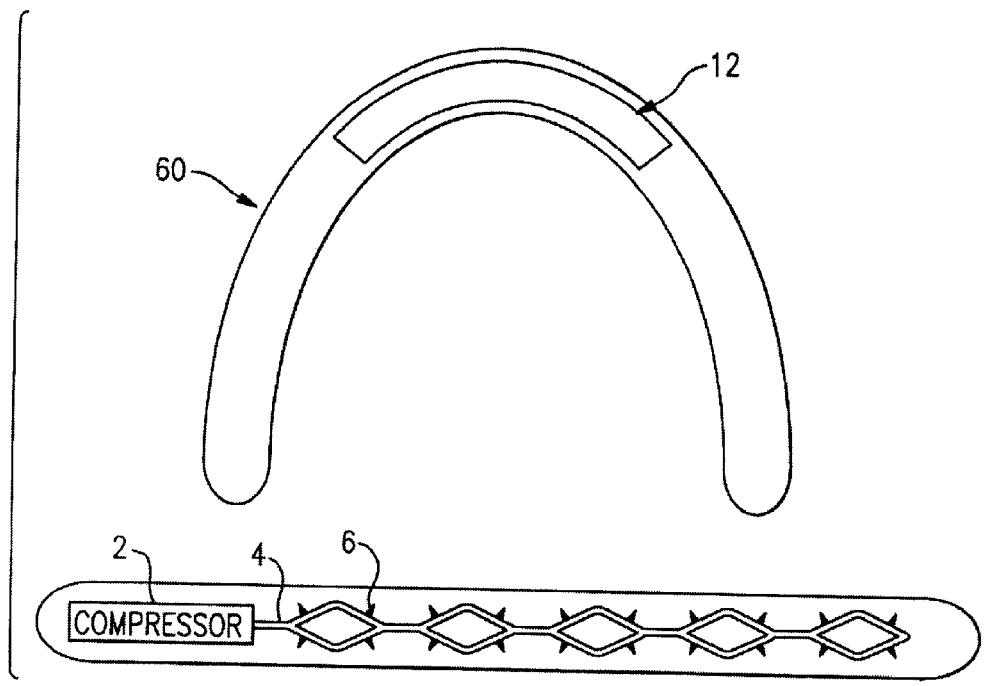
FIG. 4 is a perspective view of the present invention in use with a headband/hairband.
Figure 5:
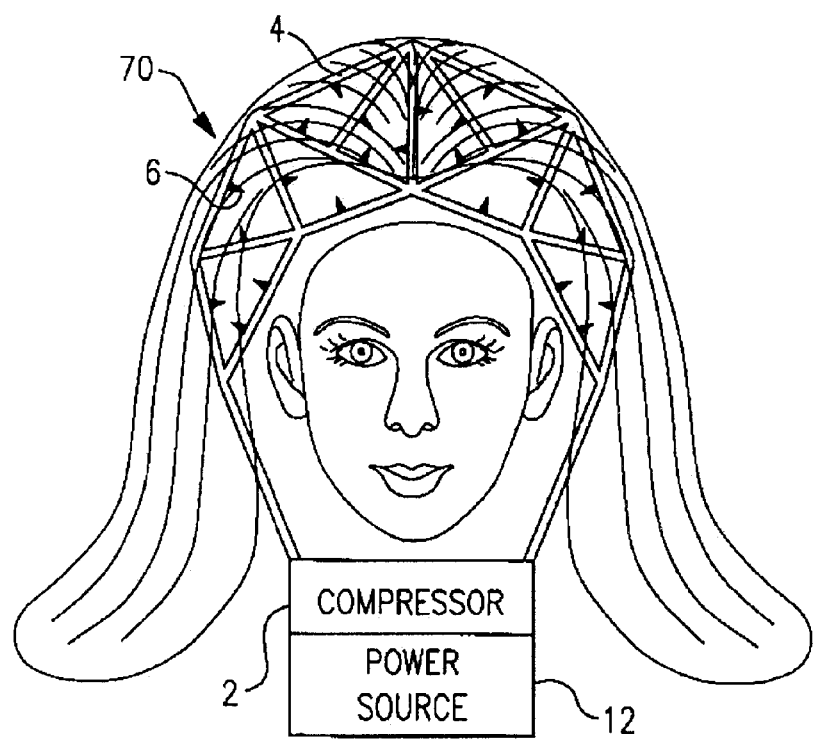
FIG. 5 is a perspective view of the present invention in use with a wig.
Figure 6:
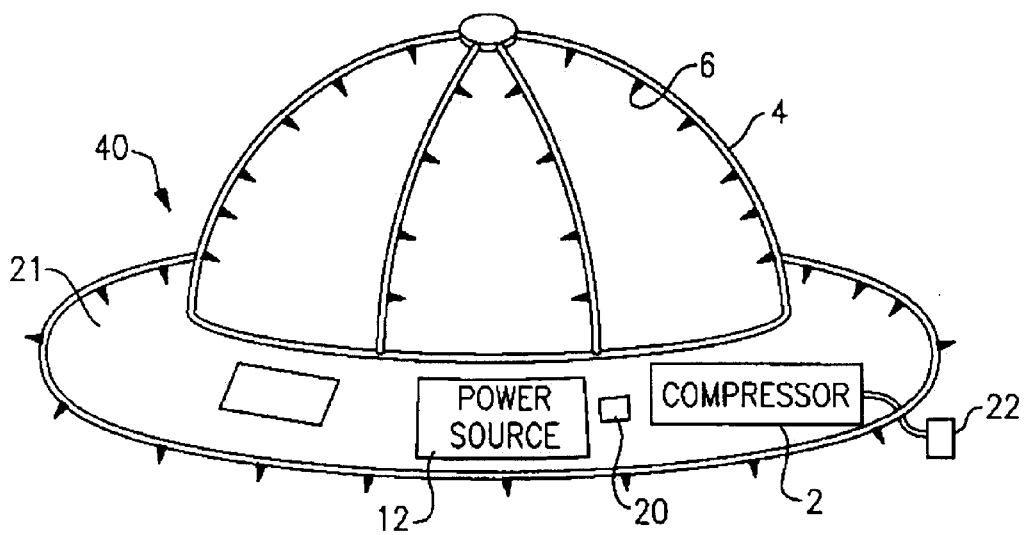
FIG. 6 is a perspective view of the present invention in use with a hardhat.

Embodiments of the present invention which optionally may not include a filter are shown in FIG. 4, which illustrates a headband or hair band 60. FIG. 5 shows an embodiment of the present invention in which the cooling system 1 is incorporated into a wig 70. The compressor 2 and power means 12 can be located on the back lower portion of the wig 70 cap.

Figure 7:
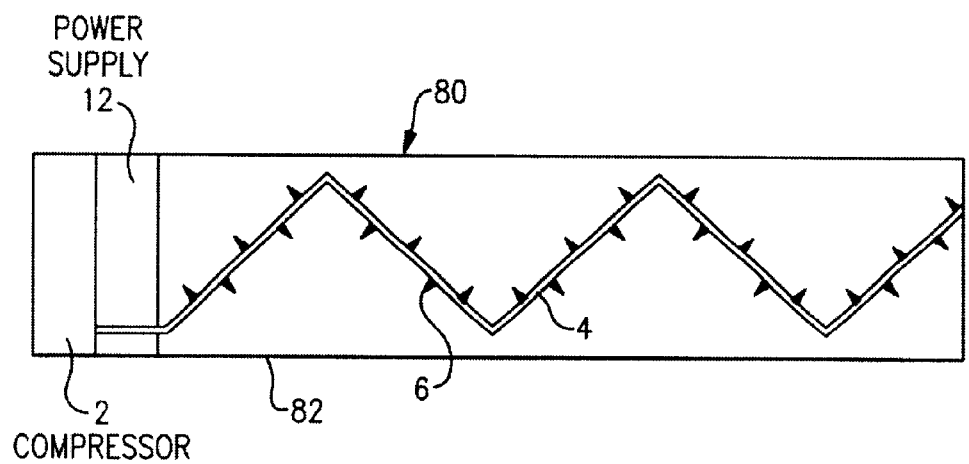
FIG. 7 is a perspective view of the present invention in use with a turbin/headwrap.
Figure 8:
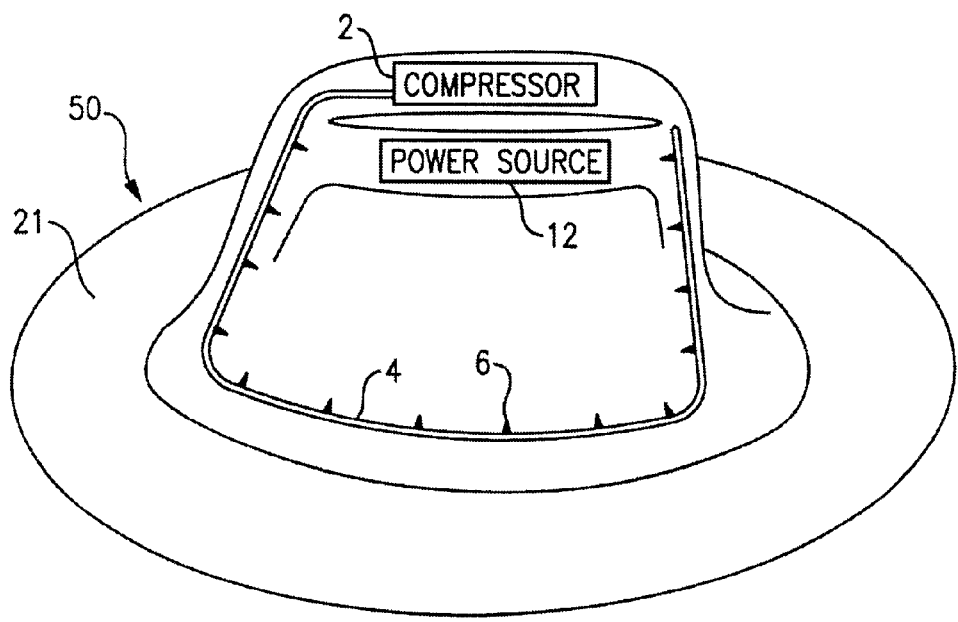
FIG. 8 is a perspective view of the present invention in use with a cowboy hat.

FIG. 7 shows an embodiment of a cooling system 80 incorporated into a fabric strip 82 for use in a turban or other headwrap. The strip 80 can be wrapped around the head and then the turban or other headwrap is wrapped or fitted thereover.

What I claim as my invention is:

1. A headgear cooling system comprising:
   a A piece of headgear, the piece of headgear having an inner-surface and an outer surface,
   b a plurality of hollow plastic tubes, each hollow plastic tube being connected to at least one other hollow plastic tube within the plurality of hollow plastic tubes, the plurality of hollow plastic tubes being attached to the inner surface of the piece of headgear, each tube having a plurality of air outlet holes spaced along said tube, the plurality of air outlet holes all facing in a direction away from the inner surface of the piece of headgear, c an air compressor unit, the -air compressor unit having an air intake tube to gather outside air or atmospheric air, the air compressor unit being connected to at least one of the plurality of hollow plastic tubes, the air compressor unit having a means to pump outside air or atmospheric air gathered through the intake air tube into the plurality of hollow plastic tubes, the air compressor unit having an external on/off switch, the air-compressor unit being mounted either on the inner surface or the outer surface of the piece of headgear, d a power means, the power means being mounted to either the inner surface or the outer surface of the piece of headgear, e an electronic connection, the electronic connection connecting the power means to the air compressor unit, f whereby a user could place the on/off switch into the "on" position, whereby the power from the power means would travel along the electronic connection to the air compressor unit, whereby the air compressor unit would suck in the outside air or atmospheric air and disperse said outside air or atmospheric air into the plurality of hollow plastic tubes, whereby the outside air or atmospheric air would exit through the plurality of air outlet holes of each tube.

2. A headgear cooling system according to claim 1, wherein the plurality of hollow plastic tubes serves as a skeletal framework for the piece of headgear.

3. A headgear cooling system comprising:

a. a piece of headgear, the piece of headgear having an inner surface and an outer surface;

b. a plurality of hollow plastic tubes, each hollow plastic tube being connected to at least one other hollow plastic tube within the plurality of hollow plastic tubes, the plurality of hollow plastic tubes being attached to the inner surface of the piece of headgear, the plurality of hollow plastic tubes having a plurality of air outlet holes, the plurality of air outlet holes all facing in a direction away from the inner surface of the piece of headgear;

c. an air compressor unit, the air compressor unit having an air intake tube to gather outside air or atmospheric air, the air compressor unit being connected to at least one of the plurality of hollow plastic tubes, the air compressor unit having a means to pump outside air or atmospheric air gathered through the intake air tube into the plurality of hollow plastic tubes, the air compressor unit having an external on/off switch, the air compressor unit being mounted either on the inner surface or the outer surface of the piece of headgear;

d. a power means, the power means being mounted to either the inner surface or the outer surface of the piece of headgear;

e. an electronic connection, the electronic connection connecting the power means to the air compressor unit; and, f. a diverter switch, the diverter switch being attached to the air compressor unit, the diverter switch being used to divert air within the plurality of hollow plastic tubes along an alternative or supplemental pathway within the plurality of hollow plastic tubes, whereby a user could place the on/off switch into the "on" position, whereby the power from the power means would travel along the electronic connection to the air compressor unit, whereby the air compressor unit would suck in the outside air or atmospheric air and disperse said outside air or atmospheric air into the plurality of hollow plastic tubes, whereby the outside air or atmospheric air would exit through the plurality of air outlet holes.

4. A headgear cooling system according to claim 1, wherein the headgear cooling system further comprises a filter, the filter being attached to the intake air tube, the filter serving to filter outside air or atmospheric air before said air would be sucked into the air compressor unit.

5. A headgear cooling system according to claim 1, wherein the power means comprises at least one battery.

6. A headgear cooling system according to claim 1, wherein the power means comprises a mechanism for converting solar energy or light energy into electronic energy.

7. A headgear cooling system according to claim 1, wherein the piece of headgear comprises a baseball cap.

8. A headgear cooling system according to claim 1, wherein the piece of headgear comprises a helmet.

9. A headgear cooling system according to claim 1, wherein the piece of headgear comprises a welder's mask.

10. A headgear cooling system according to claim 1, wherein the piece of headgear comprises a headband/hairband.

11. A headgear cooling system according to claim 1, wherein the piece of headgear comprises a wig.

12. A headgear cooling system according to claim 1, wherein the piece of headgear comprises a hardhat.

13. A headgear cooling system according to claim 1, wherein the piece of headgear comprises a turbin/headwrap.

14. A headgear cooling system according to claim 1, wherein the piece of headgear comprises a cowboy hat.

* * * * *